United States Patent [19]

Stehrenberger et al.

[11] Patent Number: 5,269,761
[45] Date of Patent: Dec. 14, 1993

[54] SAFETY HYPODERMIC NEEDLE GUARD

[76] Inventors: Mark Stehrenberger, 2203 Las Tunas Rd., Santa Barbara, Calif. 93103; Gordon A. Herrald, 533 E. Micheltorena St., Ste. 101, Santa Barbara, Calif. 93103

[21] Appl. No.: 930,176
[22] Filed: Aug. 17, 1992
[51] Int. Cl.⁵ .............................................. A61M 5/00
[52] U.S. Cl. .................................... 604/110; 604/198; 604/263
[58] Field of Search ............... 604/192, 198, 263, 110, 604/187

[56] References Cited

U.S. PATENT DOCUMENTS

4,927,416  5/1990  Tomkiel .............................. 604/198
4,966,592  10/1990  Burns et al. ........................ 604/198

Primary Examiner—John D. Yasko
Attorney, Agent, or Firm—Christie, Parker & Hale

[57] ABSTRACT

A safety needle system has a sheath that is capable of reciprocally sliding over the exterior of a syringe to alternately cover and uncover the needle portion of the syringe. The sheath is locked over the needle by means of a locking slot and coiled spring. A dog on the needle hub engages the locking slot and is held in position in the locking slot by the coiled spring. The sheath is reciprocally slidable on the exterior of the needle of the syringe by twisting the sheath to disengage the dog from the slot and moves the dog into a guide slot so that the sheath can be moved manually to expose the needle.

38 Claims, 5 Drawing Sheets

SAFETY HYPODERMIC NEEDLE GUARD

FIELD OF THE INVENTION

This invention relates to hypodermic needle syringes, and in particular to an improved sliding protective sheath mounted on the hub of a hypodermic needle to prevent accidental needle sticks.

BACKGROUND OF THE INVENTION

The possibility of a user of a hypodermic needle syringe being accidentally stuck is a constant problem for professionals utilizing such needle syringes. Because of the possible presence of serious viruses such as hepatitis and HIV after a syringe has been used on a patient, it is important that all possible precautions be taken to prevent accidental needle sticks. Various safety sheaths have been devised to cover the needle, both before and after use. Such approaches have usually involved manually removable sheaths. Also, various types of sliding sheaths have been utilized. It is desirable that a sheath be provided that will automatically return to its shielding position whenever the user releases the sheath not requiring the user to manually deploy the sheath.

BRIEF DESCRIPTION OF THE INVENTION

The present invention provides a reciprocating sheath that is spring-biased to cover the needle of a hypodermic syringe when it is not in use. The sheath is manually retracted against the bias of the spring to uncover the needle. In the extended or unretracted position, the sheath is locked in its protective position by a plurality of locking tabs. With the sheath locked in protective position, accidental needle sticks are prevented. Only if the user manually twists the sheath and retracts it can the needle be exposed. A plurality of locking slots communicating with guide slots on the sheath are provided. Twisting of the sheath brings the locking tabs out of the locking slots and into alignment with the guide slots. Thereafter retraction of the sheath produces longitudinal movement of the sheath with the tabs engaging the guiding slots to stabilize the movement of the sheath. At the same time the coil wire spring which normally holds the sheath in a locked position is compressed. The coil spring is attached to the needle hub and to the distal end of the sheath providing both axial and rotary restoring forces. The coil spring is attached to the end adjacent the needle hub by a hole in a needle adaptor mounted on the hub and at the other end to the distal end of the sheath. After the operator has finished using the syringe, the sheath is released and the biasing spring returns the sheath to its extended position over the needle and twists the sheath causing the tabs to re-engage the locking slots. In this position the sheath cannot retract or reciprocate.

An additional locking slot is provided in the proximal end of the sheath. Placing longitudinal pressure on the sheath away from the syringe compresses a set of biasing leaf springs allowing the sheath to be twisted to position the locking tabs in the permanent locking slots. The locking tabs clear the leaf springs permitting them to return to their normal unbiased position locking the tab in the permanent locked position. Thereafter, even the most severe pressure on the sheath will not move it. This is particularly important to persons who must remove waste and trash from a hospital or doctor's office. The permanently locked sheath will enable manual pickup of spent syringes, if this is necessary or desirable.

DESCRIPTION OF THE DRAWINGS

The foregoing invention will be more fully understood by reference to the drawings provided herein wherein.

DETAILED DESCRIPTION

Figure 1:
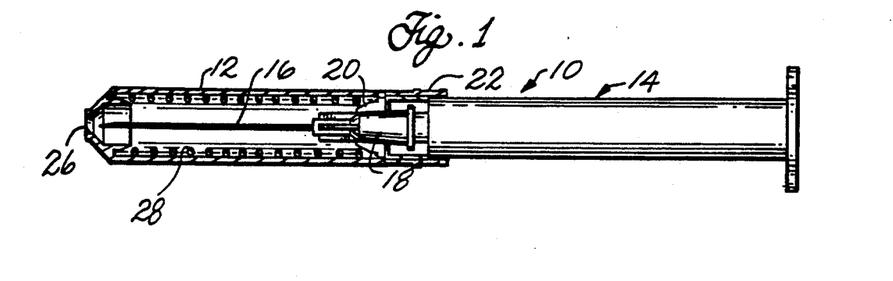
FIG. 1 is a section view of a safety hypodermic syringe system according to the present invention having a safety sheath in the fully extended position.

A safety syringe 10 according to the present invention is shown in sectional view in FIG. 1. The system 10 shown in FIG. 1 consists of sheath 12 and syringe 14. The syringe includes a needle 16 and a hub 18 which mounts the needle and joins the syringe to the needle. An adaptor 20 is mounted on hub 18 and provides the mechanism for mounting sheath 12 on a retrofit basis for the safety syringe system. The sheath 12 has a diameter slightly larger than the diameter of the syringe 14 to permit reciprocal sliding movement along the barrel of the syringe. An elongated helical spring 28 is located interiorly of the sheath. Attached to the proximal end of the sheath is a tail piece 22 which is attached to the base of the sheath and similarly has a diameter to permit sliding reciprocation along the barrel of the syringe. The sheath has a hollow interior which tapers at its distal end 24 to a narrow opening 26 which permits the needle 16 to pass when the sheath is retracted.

Figure 2:
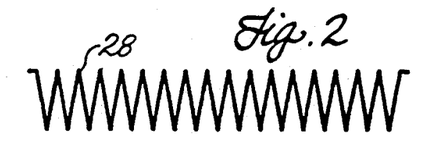
FIG. 2 is a elevation view of a coil spring used to control the safety sheath.

An enlarged view of helical wire spring 28 is shown in FIG. 2. The wire spring is preferably made of a small diameter wire having a constant spring tension. As will be more fully described, wire spring 28 is attached at the end thereof adjacent the syringe to the adaptor and at its opposite end to the distal end of the sheath. Wire spring 28 provides a circumferential biasing force as well as a longitudinal biasing force, as will be more fully discussed.

Figure 11:
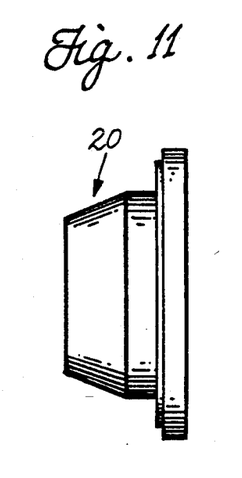
FIG. 11 is a side elevation view of one embodiment of a needle adaptor according to the present invention.

A enlarged view of the needle adaptor 20 is shown in FIG. 11. A feature of the present invention is its ability to provide a safety sheath on a retrofit basis for various hypodermic needle systems, including Terumo, Monoject and Becton-Dickenson. Since each needle syringe from each manufacturer has a slightly different configuration and dimensioning, the adaptor 20 is selected to be mounted on the needle hub for a specific model of needle and to thereafter to be fitted to the safety sheath as will be more clearly delineated in conjunction with the discussion of FIGS. 8A to 8I.

Figure 5:
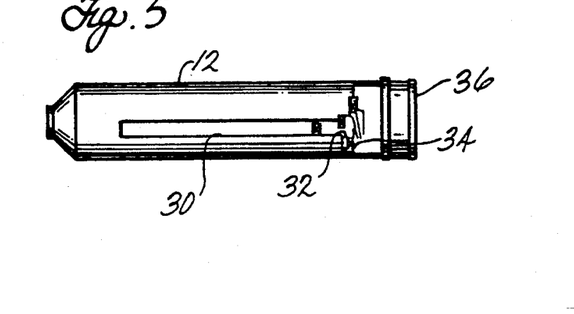
FIG. 5 is an elevation view of the safety sheath and tail-piece assembly.

The structure in FIG. 5 shows a safety sheath 12 having a guide slot 30 and a locking slot 32. In the preferred embodiment of the sheath, three guide slots 30 and three locking slots 32 are provided at spaced intervals around the circumference of the sheath. As is shown in FIG. 5, a tab 34 on the hub is sized and positioned so as to engage locking slot 32 and guide slot 30 when the sheath is put into operation. Under the normal circumferential biasing force of wire spring 28, sheath 12 is held and the syringe is twisted in a clockwise direction so as to cause tab 34 to engage locking slot 32. When the needle is to be used, the syringe is twisted in a clockwise manner so that tab 34 moves into alignment with the guide slot 30. Upon retraction against the longitudinal biasing force of the wire spring 28 by the user, the tabs 34 engage guiding slots 30, and the sheath is pulled back and held by the user to expose a needle and place the syringe in condition for permitting the injection to be made into the patient.

Figure 7:
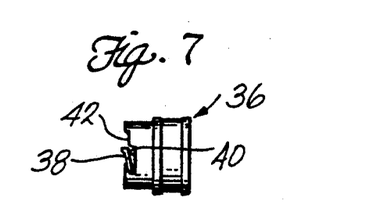
FIG. 7 is sectional view of the syringe with the sheath retracted.

As the elevational views in FIGS. 5 and 7 show, a tail piece 36 is attached to the proximal end of the sheath 12. The tail piece is provided with a molded plastic leaf spring 38 at three intervals around the circumference of the tail piece. The leaf spring 38 provides permanent locking of the sheath after use of the syringe. This permanent locking is accomplished by allowing the sheath to be extended to its normal shielding position, completely encompassing the needle. In this condition, if the user releases the sheath, tab 34 slides into and locks the sheath in locking slots 32. To provide a permanent lock of the sheath on the needle, the syringe is twisted clockwise and pulled longitudinally away from the sheath so as to compress leaf springs 38 into recesses 40. Further twisting of the sheath urges tab 34 into detent 42 on tail piece 36 providing clearance for leaf spring 38 to snap back into its uncompressed position and to engage tab 34, thereby permanently locking tab 34 in detent 42.

Figure 3:
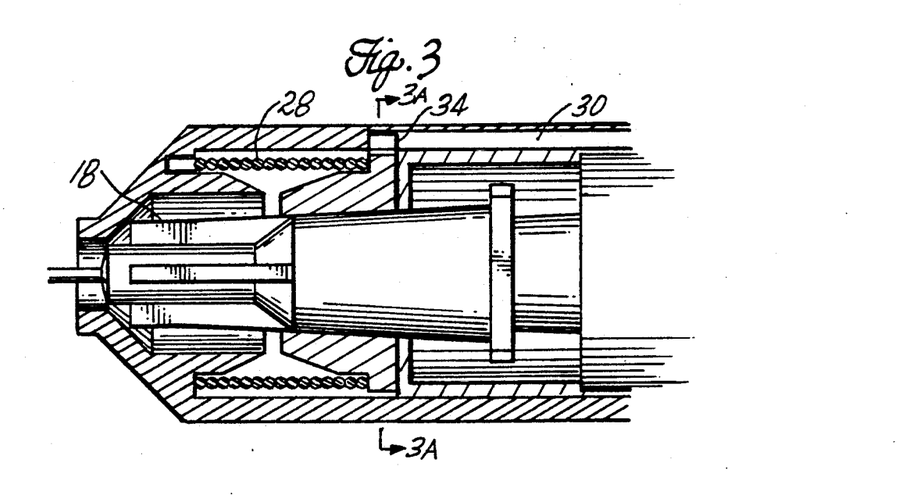
FIG. 3 is an enlarged view of the needle hub assembly with the sheath retracted.
Figure 4A:
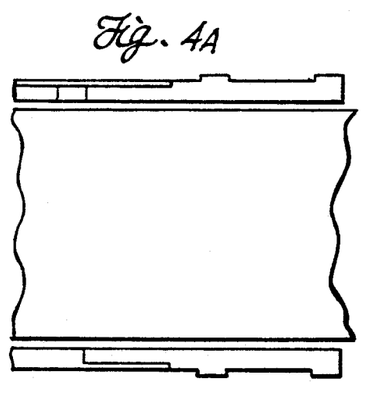
FIG. 4A is a partial sectional view of the rear portion of the safety sheath and the tail piece.
Figure 4B:
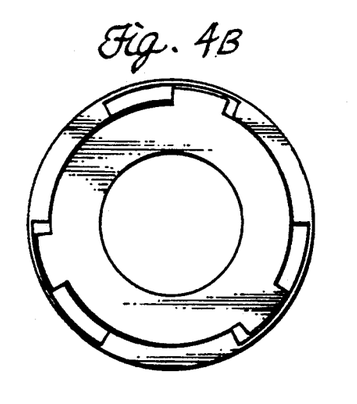
FIG. 4B is a sectional view taken along lines 3A—3A of FIG. 3.
Figure 6:
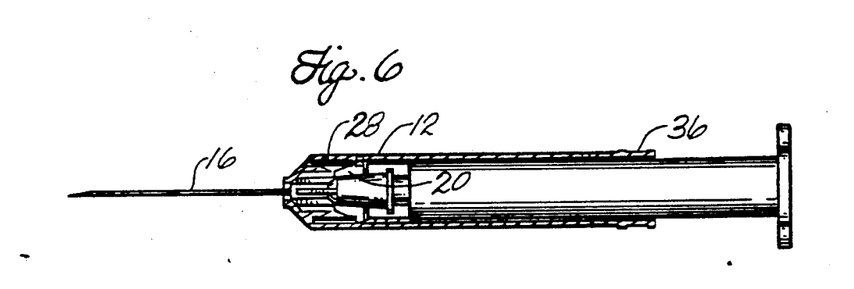
FIG. 6 is an elevation view of a tail piece.

The operation of the syringe will be further understood by reference to FIGS. 3 and 6. As shown in FIG. 3 and 6, sheath 12 is in the fully retracted position exposing needle 16 for use with a patient. Wire spring 28 is shown in FIG. 6 as a heavy black line extending from an interior point at the beginning taper of sheath 12 to the point of attachment on adaptor 20. As shown in FIGS. 3 and 6, spring 28 is fully compressed. The interior tapered portion of the sheath rests and bears against the needle hub 18 in the fully retracted position. The fully compressed condition of spring 28 is shown in the enlarged exploded view of FIG. 6. As seen therein, tab 34 is located in guide slot 30, and is likewise bearing against the distal end of the guide slot when the sheath is fully retracted and wire spring 28 fully compressed. The user holds the sheath between the fingers of one hand while inserting the needle into a bottle of medication to withdraw the measured quantity into the barrel of the syringe. The user continues to hold the sheath while the needle is brought into position with respect to the patient to administer the medication. Similarly the sheath is held by the user in the retracted position when blood samples taken from a patient's vein.

Figure 8A:
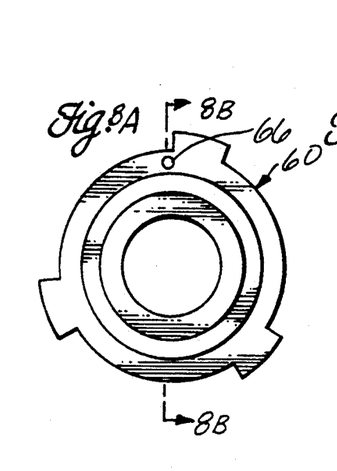
FIG. 8A is a top plan view of a first embodiment of a needle adaptor.
Figure 8B:
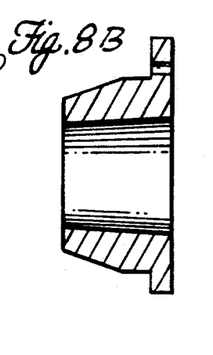
FIG. 8B is a sectional view of the adaptor taken along lines 8B—8B of FIG. 8A.
Figure 8C:
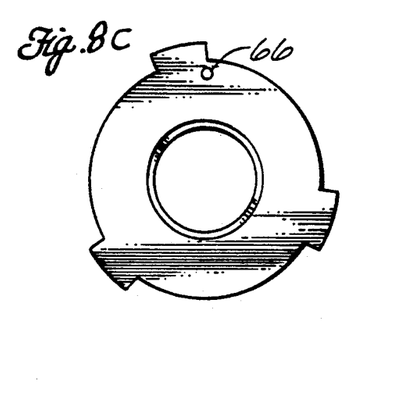
FIG. 8C is a bottom plan view of the adaptor of FIG. 8A.
Figure 8D:
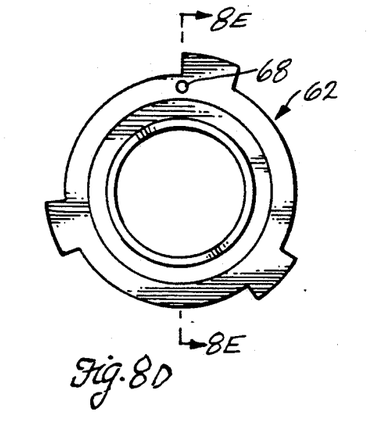
FIG. 8D is a top plan view of a second embodiment of an adaptor.
Figure 8E:
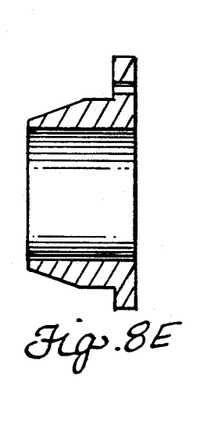
FIG. 8E is a sectional view of the adaptor of FIG. 8D.
Figure 8F:
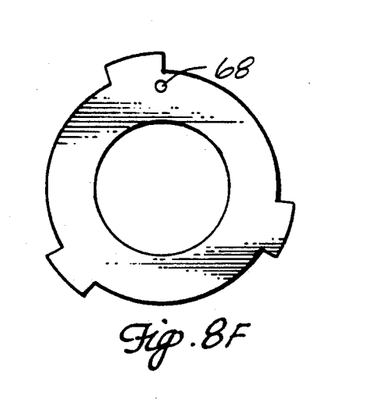
FIG. 8F is a bottom plan view of the adaptor of FIG. 8D.
Figure 8G:
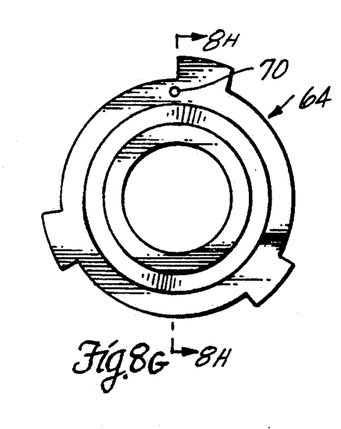
FIG. 8G is a top plan view of a third embodiment of an adaptor.
Figure 8H:
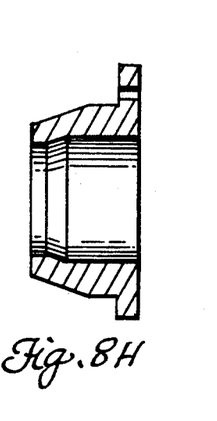
FIG. 8H is a sectional plan view of the adaptor of FIG. 8G.
Figure 8I:
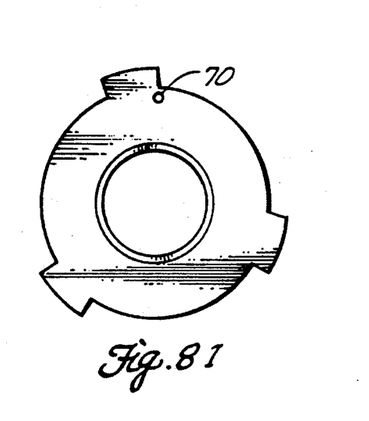
FIG. 8I is a bottom plan view of the adaptor of FIG. 8G.

The system according to the present invention is adaptable to many syringe designs currently available. As shown in FIGS. 8A, 8B, 8C, an adaptor 60 shown therein is suitable for retrofitting a Becton-Dickenson syringe. Similarly the adaptor 62 shown in FIGS. 8D, 8E, 8F is designed to retrofit the safety sheath system of the present invention to a Monoject syringe. As shown in FIGS. 8G, 8H, 8I, the adaptor 64 is designed so as the retrofit a Terumo syringe with the safety sheath according to the present invention. Apertures 66, 68, 70 shown in FIGS. 8A, 8C, 8D, 8F, 8G and 8I are the apertures engaged by the helical spring utilized with the safety sheath.

Figure 9A:
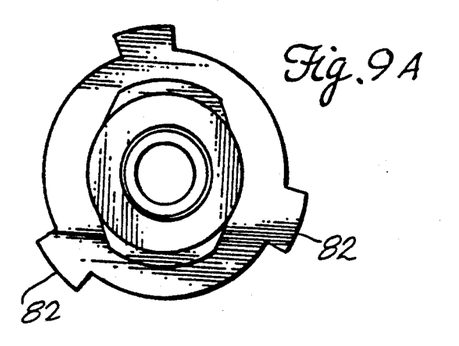
FIG. 9A is a schematic sectional view of a needle hub, with integrated adaptor.
Figure 9B:
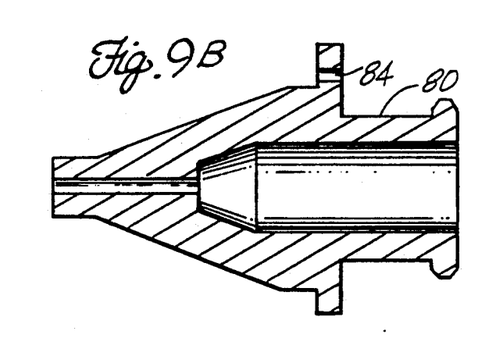
FIG. 9B is a rear elevation view of a syringe with the needle hub and integrated adaptor.
Figure 10A:
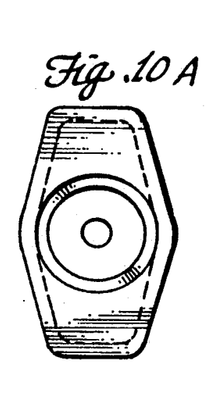
FIG. 10A is a rear elevation view syringe with the safety sheath fully integrated into the syringe according to the present invention.
Figure 10B:
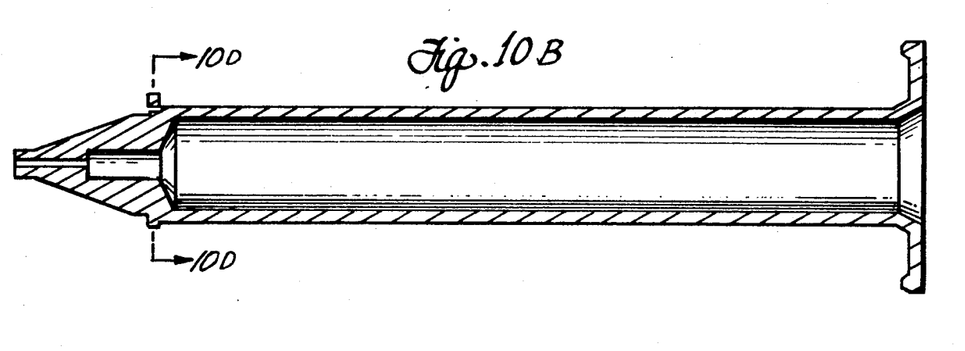
FIG. 10B is a sectional view taken along lines 10B—10B of FIG. 10A.
Figure 10C:
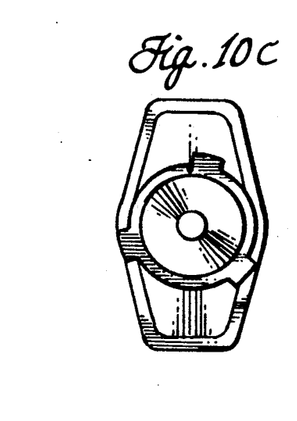
FIG. 10C is a front elevation view of the integrated syringe shown in FIG. 10A.
Figure 10D:
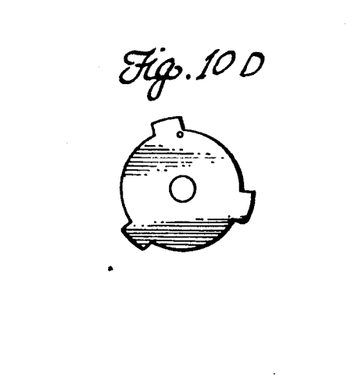
FIG. 10D is a section view taken along lines 10D—10D of FIG. 10B.

As indicated above, the adaptor and sheath can be integrated into one structure as shown in FIGS. 9A and 9B. In the elevation view of FIG. 9A, the adaptor and hub are molded in one piece 80. An aperture 82 is provided for the syringe needle. Locking tabs 84 are provided around the periphery of the hub and an aperture 86 is provided for securing the proximal end of the helical spring.

Finally as shown in FIGS. 10A, 10B, 10C, 10D, the safety sheath system according to the present invention is shown fully integrated into the syringe design. In this embodiment the hub, adaptor and syringe barrel are molded in one piece. Locking tabs and a helical coil spring aperture are also provided.

Thus, the invention provides an elegant and simple design of safety sheath for a safety needle system which can either be attached to a needle hub on a retrofit basis or can integrated with the needle hub on an original equipment manufacturer basis. In either event, positive locking of the shield in the extended position, and positive guiding of the sheath as it is being retracted and extended, is provided by the design of the present invention. The design provides for automatic return of the sheath to its locked position by utilization of the wire spring which provides both longitudinal biasing and circumferential biasing. Finally, the minimal number of parts and the molded nature of the elements that are used in the safety sheath provide for a safety sheath system that is low in cost to manufacture and hence does not add significantly to the cost of the hypodermic needle thereby making it even more suitable for use in this day and age of constant danger of accidental needle stick infections.

What is claimed is:

1. A safety automatically self-closing needle system comprising:
    a hypodermic syringe having a tubular barrel, a needle and a needle hub joining the needle to the barrel;
    a tubular safety sheath disposed about syringe, the sheath having a first open end, a diameter such as to slidably encompass the barrel and a small central opening at the opposite end to pass the needle;
    at least one lateral slot located in the wall of the sheath adjacent the first open end of the sheath;
    at least one guide slot located in the wall of the sheath extending longitudinally thereof and opening at right angles into the lateral slot;
    pin means mounted on the hub for engaging the lateral slot and guide slot;
    rotational and axial biasing means located interiorly of the sheath engaging the syringe at the first open end of the sheath and the interior of the sheath at the opposite end thereof whereby at rest the biasing means locks the pin means in the locking slot and in operation, rotational movement of the sheath against rotational biasing force moves the tab out of the locking slot and into the guide slot to permit retraction of the sheath against axial biasing force.

2. The system according to claim 1 wherein the rotational and axial biasing means is a compression spring secured at one end to the hub and at the opposite end to the sheath.

3. The system according to claim 2 wherein a plurality of guide slots and associated locking slots are provided at regularly spaced intervals in the wall of the sheath.

4. The system according to claim 3 wherein the pin means are provided extending from the hub for engaging the lateral and guide slots.

5. A system according to claims 4 including means for permanently locking the sheath in the extended position after use.

6. A safety needle system comprising
    a hypodermic syringe having a tubular barrel, and a needle joined to the barrel;
    a tubular safety sheath adopted to be attached to the syringe, the sheath having a first open end, a diameter such as to slidably encompass the barrel and a small central opening at the opposite end to pass the needle;
    a guide slot located in the wall of the sheath extending longitudinally thereof,
    a laterally extending locking slot located in the wall of the sheath adjacent the open end of the sheath in communication with the guide slot;
    means mounted on the syringe for engaging the locking slot and guide slot;
    biasing means located interiorly of the sheath connected to the syringe at one end and to the interior of the sheath at the opposite end for providing rotational and longitudinal bias of the sheath whereby at rest, the biasing means rotationally biases the engaging means into the locking slot and in operation, a twisting motion of the sheath against biasing tension moves the engaging means into the guide slot and out of the locking slot to permit retraction of the sheath against the longitudinal bias of the biasing means.

7. The system according to claim 1 wherein a plurality of longitudinal guide slots are located at spaced intervals in the wall of the sheath.

8. The system according to claim 7 wherein a laterally extending locking slot is provided at spaced intervals in the wall of the sheath in communication with a respective one of said guide slot.

9. The system according to claim 8 including locking means at the first open end of the sheath.

10. A system according to claims 9 wherein the locking means includes a compressible locking tab for permanently locking the sheath in the extended position after use.

11. A safety needle system comprising
    an integrated hypodermic syringe comprising a tubular barrel and a hypodermic needle integrally formed with the barrel and communicating with the interior of the barrel;
    a tubular safety sheath adapted to be attached to the syringe, the sheath having a first open end for receiving the tubular barrel, a diameter such as to slidably encompass the barrel and a small central opening at the opposite end to pass the needle;
    a guide slot located in the wall of the sheath extending longitudinally thereof,
    a laterally extending locking slot located in the wall of the sheath adjacent the open end of the sheath in communication with the guide slot;
    pin means on the exterior of the syringe for engaging the locking slot and guide slot; and
    spring means located interiorly of the sheath connected to the syringe at one end and to the sheath at the opposite end for providing rotational and longitudinal bias of the sheath whereby at rest the spring means automatically rotationally biases the pin means into the locking slot and in operation, a twisting motion of the sheath against spring tension moves the pin means into the guide slot and out of the locking slot to permit retraction of the sheath against the longitudinal bias of the spring means.

12. The system according to claim 11 where the pin means is a tab integrally formed on the hub.

13. The system according to claim 12 wherein a plurality of longitudinally guide slots are located at spaced intervals in the wall of the sheath.

14. The system according to claim 13 wherein a laterally extending locking slot is provided at spaced intervals in the wall of the sheath in communication with a respective one of said guide slots.

15. The system according to claim 14 including locking means at the first open end of the sheath.

16. A system according to claims 15 wherein the locking means includes a compressible locking tab for permanently locking the sheath in the extended position after use.

17. A safety needle system comprising
    a hypodermic syringe comprising a tubular barrel, a detachable hypodermic needle and hub assembly and fitting means for joining the needle and the hub assemble to the barrel, the needle communicating with the interior of the barrel;
    a tubular safety sheath adapted to be attached to the syringe, the sheath having a first open end for receiving the tubular barrel, a diameter such as to slidably encompass the barrel and a small central opening at the opposite end to pass the needle;
    a guide slot located in the wall of the sheath extending longitudinally thereof, a laterally extending locking slot located in the wall of the sheath adjacent the open end of the sheath in communication with the guide slot;

means integrally formed on the hub for engaging the locking slot and guide slot; and spring means located interiorly of the sheath connected to the hub at one end and to the sheath at the opposite end for providing rotational and longitudinal bias of the sheath whereby at rest the spring means automatically rotationally biases the engaging means into the locking slot and in operation, a twisting motion of the sheath against spring tension moves the engaging means into the guide slot and out of the locking slot to permit retraction of the sheath against the longitudinal bias of the spring means.

18. The system according to claim 17 where the engaging means is a tab integrally formed on the syringe adjacent the junction between the needle and the barrel.

19. The system according to claim 18 wherein a plurality of longitudinal guide slots are located at spaced intervals in the wall of the sheath.

20. The system according to claim 19 wherein a laterally extending locking slot is provided at spaced intervals in the wall of the sheath in communication with a respective one of said guide slots.

21. The system according to claim 20 including locking means to the first open end of the sheath.

22. A system according to claims 21 wherein the locking means includes a compressible locking tab for permanently locking the sheath in the extended position after use.

23. A retrofitted safety needle system comprising
a hypodermic syringe having a tubular barrel, a detachable hypodermic needle and hub assembly and fitting means joining the needle and hub assembly to the barrel, the needle communicating with the interior of the barrel;
a tubular safety sheath adapted to be attached to the syringe, the sheath having a first open end, a diameter such as to slidably encompass the barrel and a small central opening at the opposite end to pass the needle;
an adapter collar for being circumferentially mounted on the needle and hub assembly to permit a safety sheath to be retrofitted to currently available syringe assemblies;
a guide slot located in the wall of the sheath extending longitudinally thereof,
a laterally extending locking slot located in the wall of the sheath adjacent the open end of the sheath in communication with the guide slot;
means mounted on the adapted for engaging the locking slot and guide slot; and
spring means located interiorly of the sheath connected to the adapter collar at one end and to the sheath at the opposite end for providing rotational and longitudinal bias of the sheath whereby at rest the spring means automatically rotationally biases the engaging means into the locking slot and in operation, a twisting motion of the sheath against spring tension moves the engaging means into the guide slot and out of the locking slot to permit retraction of the sheath against the longitudinal bias of the spring means.

24. The system according to claim 23 where the engaging means is a tab integrally formed on the adapter collar.

25. The system according to claim 24 wherein a plurality of longitudinal guide slots are located at spaced intervals in the wall of the sheath.

26. The system according to claim 25 wherein a laterally extending locking slot is provided at spaced intervals in the wall of the sheath in communication with a respective one of said guide slots.

27. The system according to claim 26 including locking means at the first open end of the sheath.

28. A system according to claims 27 wherein the locking means includes a compressible locking tab for permanently locking the sheath in the extended position after use.

29. In a safety needle system utilizing a tubular barrel, and fitting means for receiving and joining a hypodermic needle and hub assembly to the barrel to provide a hypodermic syringe, the improvement comprising
a tubular safety sheath adapted to be attached to the needle system, the sheath having a first open end for receiving the tubular barrel, a diameter such as to slidably encompass the barrel and a small central opening at the opposite end to pass the needle;
a guide slot located in the wall of the sheath extending longitudinally thereof,
a laterally extending locking slot located in the wall of the sheath adjacent the open end of the sheath in communication with the guide slot;
means integrally formed on the hub for engaging the locking slot and guide slot; and
biasing means located interiorly of the sheath connected to the hub at one end and to the sheath at the opposite end for providing rotational and longitudinal bias of the sheath whereby at rest, the biasing means rotationally biases the engaging means into the locking slot and in operation, a twisting motion of the sheath against biasing force moves the engaging means into the guide slot and out of the locking slot to permit retraction of the sheath against the longitudinal bias of the biasing means.

30. The system according to claim 1 wherein a plurality of longitudinal guide slots are located at spaced intervals in the wall of the sheath.

31. The system according to claim 7 wherein a laterally extending locking slot is provided at spaced intervals in the wall of the sheath in communication with a respective one of said guide slots.

32. The system according to claim 8 including locking means at the first open end of the sheath.

33. A system according to claims 9 wherein the locking means includes a compressible locking tab for locking the sheath in the extended position after use.

34. In a safety needle system utilizing a tubular barrel, a detachable hypodermic needle and hub assembly and fitting means joining the needle and hub assembly to the barrel to provide a hypodermic syringe, the improvement comprising
a tubular safety sheath adapted to be attached to the needle system, the sheath having a first open end, a diameter such as to slidably encompass the barrel and a small central opening at the opposite end to pass the needle;
an adapter collar for being circumferentially mounted on the needle and hub assembly to permit a safety sheath to be retrofitted to currently available hypodermic syringes;
a guide slot located in the wall of the sheath extending longitudinally thereof, a laterally extending locking slot located in the wall of the sheath adjacent the open end of the sheath in communication with the guide slot;

means mounted on the adapter collar for engaging the locking slot and guide slot; and biasing means located interiorly of the sheath connected to the adapter collar at one end and to the sheath at the opposite end for providing rotational and longitudinal bias of the sheath whereby at rest the biasing means rotationally biases the engaging means into the locking slot and in operation, a twisting motion of the sheath against biasing force moves the engaging means into the guide slot and out of the locking slot to permit retraction of the sheath against the longitudinal bias of the spring.

35. The system according to claim 1 wherein a plurality of longitudinal guide slots are located at spaced intervals in the wall of the sheath.

36. The system according to claim 7 wherein a laterally extending locking slot is provided at spaced intervals in the wall of the sheath in communication with a respective one of said guide slots.

37. The system according to claim 8 including locking means at the first open end of the sheath.

38. A system according to claims 9 wherein the locking means includes a compressible locking tab for locking the sheath in the extended position after use.

* * * * *